(12) United States Patent
Lee et al.

(10) Patent No.: US 6,569,978 B2
(45) Date of Patent: May 27, 2003

(54) ANIONIC POLYMERIZATION OF FUNCTIONALIZED STYRENE DERIVATIVES CONTAINING CARBAZOLE

(75) Inventors: Jae Suk Lee, Kwangju (KR); Young Sun Cho, Kwangju (KR); Chi Sung Ihn, Kwangju (KR); Hye Kyung Lee, Kwangju (KR)

(73) Assignee: Kwangju Institute of Science and Technology, Kwangju (KR)

( * ) Notice: Subject to any disclaimer, the term of this patent is extended or adjusted under 35 U.S.C. 154(b) by 0 days.

(21) Appl. No.: 09/862,336

(22) Filed: May 23, 2001

(65) Prior Publication Data

US 2002/0115810 A1 Aug. 22, 2002

(30) Foreign Application Priority Data

Dec. 19, 2000 (KR) ........................................ 2000-78168

(51) Int. Cl.$^7$ .............................................. C08F 212/06
(52) U.S. Cl. ...................... 526/347; 526/259; 526/263; 526/328.5
(58) Field of Search ............................... 526/259, 263, 526/328.5, 347

(56) References Cited

PUBLICATIONS

Gibson et al., Macromolecules (1977), 10(3), 602–4.*
Chiellini et al., Polym. Bull. (Berlin) (1980), 2(8), 577–87.*
Solaro et al., Eur. Polym. J. (1983), 19(5), 433–8.*
Y. Zhang, et al., "A New Synthetic Approach to Macrocyclic Molecules and Main–Chain Polymers Containing Carbazole Moieties", Chem. Commun., 1996, pp. 621–622.
K. Tamura, "New Polymeric Material Containing the Tri-cyanovinyl–carbazole Group for Photorefractive Applications", Applied Physics Letters, vol. 60, No. 15, Apr. 13, 1992, pp. 1803–1805.
Y. Zhang, "One–Pot Synthesis of a New Hyperbranched Polyester Containing 3,6–di–acceptor–substituted Carbazole Chromophores for Nonlinear Optics", Macromol. Chem. Phys., 1996, pp. 667–676.
A. Ribou, et al., "Synthesis, Characterization and Optical Properties of Novel Carbazole–Ruthenium Compounds: Carbazole as a New Building Block?", Inorganica Chimica Acta, vol. 288, 1999, pp. 134–141.
T. Ishizone, et al., "Anionic Polymerization of Monomers Containing Functional Groups.10.Anionic Polymerizations of N–Aryl–N–(4–vinyl–benzylidene)amines", Macromolecules, vol. 30, No. 21, 1997, pp. 6458–6466.
T. Ishizone, et al., Anionic Polymerization of Monomers Containing Functional Groups 13.Anionic Polymerizations of 2–,3–,and 4–(3,3–Dimethyl–1–butynyl)styrenes, 2–,3–, and 4–(1–Hexnyl)styrenes, and 4–(Phenylethynyl)styrene, Macrolecules, vol. 31, No. 12, 1998, pp. 3764–3774.

* cited by examiner

Primary Examiner—Helen L. Pezzuto
(74) Attorney, Agent, or Firm—Rosenberg, Klein & Lee

(57) ABSTRACT

Disclosed are functionalized styrene derivatives containing carbazole and their anionic polymerization. Styrene derivatives containing carbazole, and homopolymers or copolymers of the styrene derivatives can be synthesized by the anionic polymerization method. Thusly synthesized high molecular weight polymer containing carbazole has advantages of thermal stability, optical properties, and defined molecular weight and limited molecular weight distribution.

6 Claims, 5 Drawing Sheets

ELECTRONEGATIVITY: N: 3.0, S: 2.5, O: 3.5

1. INITIATION

2. PROPAGATION

3. TERMINATION

ANIONIC POLYMERIZATION OF FUNCTIONALIZED STYRENE DERIVATIVES CONTAINING CARBAZOLE

BACKGROUND OF THE INVENTION

1. Field of the Invention

The present invention relates to functionalized styrene derivatives containing carbazole and their anionic polymerization. More specifically, the present invention relates to styrene derivatives containing carbazole, and an improvement in the thermal stability, optical properties, and molecular weight and molecular weight distribution of homopolymers or copolymers of the styrene derivatives, along with the anionic polymerization method. The term, optical properties, as used herein include photoluminescence and photoconductivity.

2. Description of the Prior Art

Carbazole-containing materials have been widely used as photoconductive, refractive and non-linear optical materials, and have been recently reported to be useful as media of photoluminescence materials [(1) Y. Zhang, T. Wada, and H. Sasabe, Chem. Commun., 1996, 621. (2) Y. Zhang, T. Wada, and H. Sasabe, Macromol. Chem. Phys., 1996, 197, 667. (3) K. Tamura, A. B. Padias, H. K. Hall Jr., and N. Peyghambarian, Appl. Phys. Lett., 1992, 60, 1803.].

In addition, it is reported that carbazole-containing materials, together with associated metals, have been used as polymers for electrophotoluminescence [A. Ribou, T. Wada, and H. Sasabe, Inorganica Chemica Acta, 1999, 288, 134].

The photorefractive polymers must preferably have low glass transition temperature, while the electrophotoluminescent polymers must preferably have high glass transition temperature in consideration of thermal stability. Therefore, if glass transition temperature can be controlled by the molecular weight of the polymers, the polymers can be used for various applications.

Since anionic polymerization of styrene has been found, researches have been actively carried out. Recently, anionic polymerization techniques have been developed, so styrene can be prepared in large scale through such polymerization at plants.

However, in the case of styrene with functional groups, undesirable side-reactions occur during the polymerization. In this regard, it is reported that, in styrene derivatives with functional electron donating groups to the para-position, side-reactions are caused so that molecular weight and molecular weight distribution of the polymer cannot be controlled [T. Ishizone, T. Utake, Y. Ishino, A. Hirao, and S. Nakahama, Macromolecules, 1987, 30, 6548]. Furthermore, when methylene group is introduced into styrene as a functional group, highly reactive chain ends of the polymer attack methylene group during polymerization, thus it is not easy to obtain well-controlled polymers.

Much efforts have been directed toward successfully synthesizing polymers by introducing a functional group-protecting group to the polymerization reaction, and then removing the protecting group after the polymerization [T. Ishizone, G. Uehara, A. Hirao, S. Nakahama, and K. Tsuda, Macromolecules, 1998, 31, 3764].

When monomer is in a liquid state, pure monomer can be obtained by distillation or other processes, while monomer of solid state has some impurities because distillation cannot be performed in a vacuum. Hence, such impurities reduce activity of starting materials, and consequently molecular weight and molecular weight distribution of the polymer cannot be easily controlled.

SUMMARY OF THE INVENTION

Accordingly, an object of the present invention for alleviating the problems as described above is to provide a polymer and a method for synthesizing the same, in which a carbazole-containing solid styrene monomer is used at lowered reaction temperature which restrains side-reactions, so that a homopolymer with defined molecular weight and limited molecular weight distribution is resulted, and such homopolymer and a carbazole-containing styrene derivative are block-copolymerized with other monomers, thereby obtaining a polymer with defined molecular weight.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Based on the present invention, synthesized are a homopolymer with controlled molecular weight and narrow molecular weight distribution of the monomer,4-methylcarbazolyl styrene monomer containing carbazole, and a controlled block copolymer of the monomer with styrene, methylmethacylate (MMA) or 9-ethylcarbazollyl methacrylate (CzMA).

Figure 1:
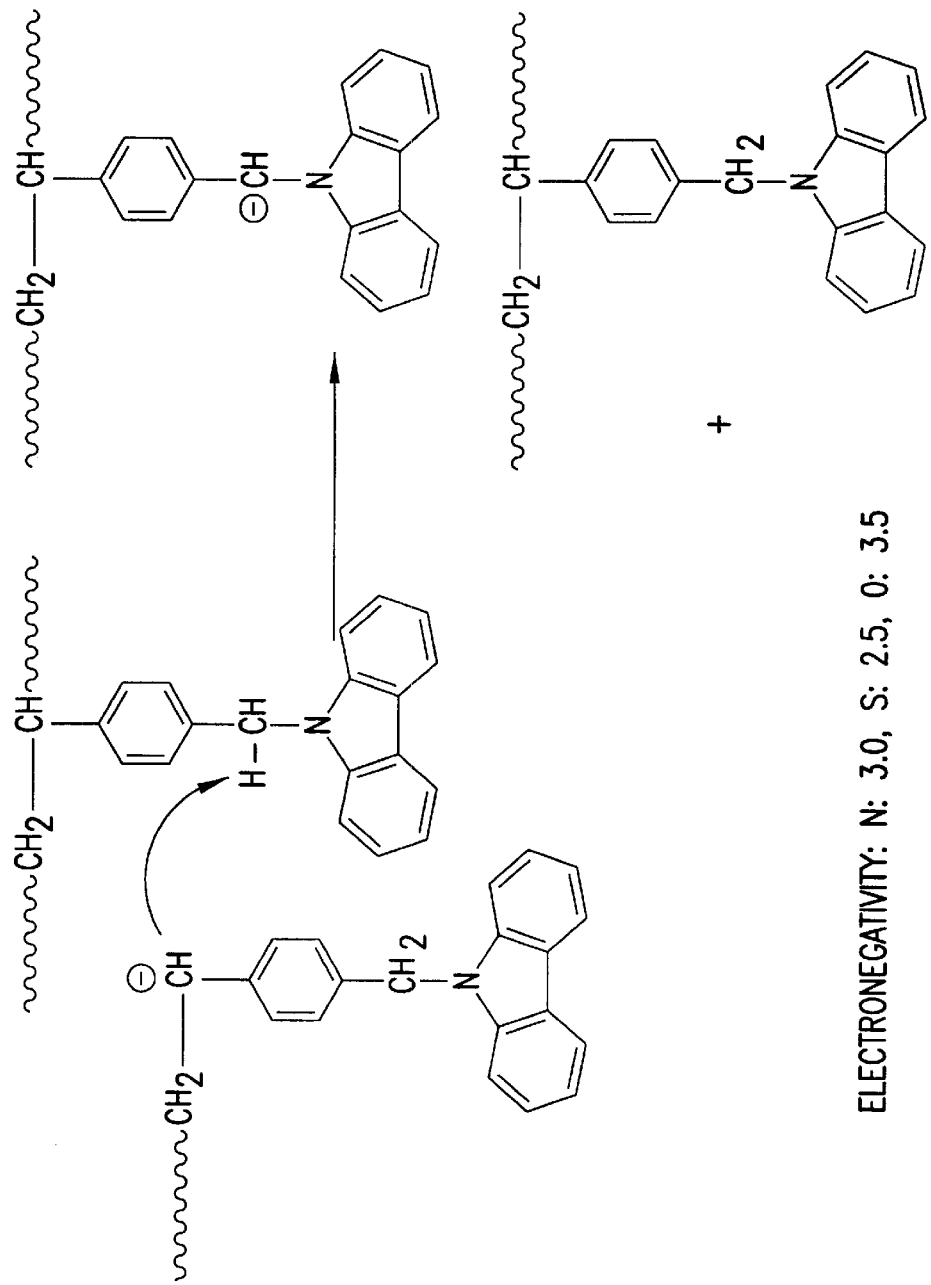
FIG. 1 shows a reaction scheme of a mechanism for undesirable side-reactions during polymerization used in the present invention.
Figure 2:
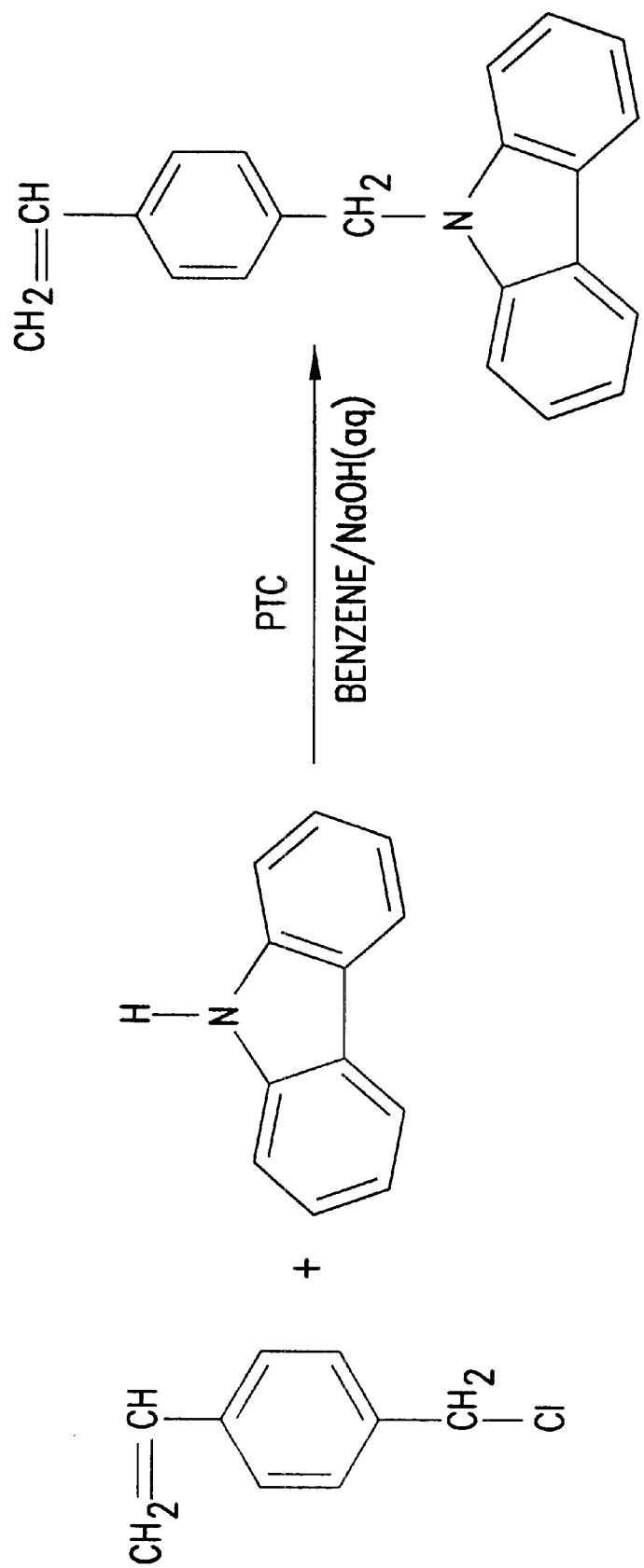
FIG. 2 shows a reaction scheme for synthesizing the carbazole-containing monomer of the present invention.

Carbazole was reacted with 1.5-fold excess of 4-vinylbenzyl chloride in benzene/water using NaOH as a base, and benzyltriethylammonium chloride as phase catalyst to afford 4-(9-carbazolyl)methylstyrene (CMS) at 80° C. for 5 h. The reaction mixture was extracted with chloroform and the organic layer washed with water, evaporated, and washed with hexane several times. The solid was dissolved in and recrystallized from diethyl ether at −20° C. Yield: 80%. The solid monomer was dried over $P_2O_5$ at 10-6 mmHg for 1 week and then dissolved in anhydrous THF and stored at −30° C. in glass ampoules under high vacuum. This reaction scheme is schematically shown in FIG. 2. The monomer is characterized by using 1H-NMR, 13C-NMR and FT-IR. Undesirable side-reaction of the monomer prepared is seen in FIG. 1.

From the monomer obtained above, poly(4-(9-carbazollylmethyl styrene)), being a homopolymer, is synthesized as follows.

Anionic polymerizations were carried out in THF under high-vacuum conditions (10-6 mmHg) for 5 min to 24 h in an all-glass apparatus equipped with break-seals in the usual manner. For the homopolymerization of CMS, a THF solution of the CMS was added to K-Naph. solution in THF at −45 or −78° C. and allowed to react for 5 min to 24 h, and then terminated with methanol. The polymers were precipitated in large amount of methanol, dried, dissolved in benzene, and freeze-dried. The yield of polymer was determined from 1H-NMR data.

The synthesis of the block copolymers is carried out by the following procedure.

Styrene was polymerized with K-Naph. in THF at −78° C. in all glass apparatus in vacuo. After 30 min, a portion of living polystyrene was withdrawn to attached receiver to determine characteristic of the homopolymer. The second monomer, CMS, in THF solution was added to the living homopolystyryl solution in THF solution, polymerized for 24 h at −78° C., terminated with methanol, and precipitated in the large amount of methanol. Also, the reverse triblock copolymer between CMS and styrene, PS-b-PCMS-b-PS (Polystyrene-Block-Carbazolylmethylstyrene-Block-Polystyrene), was synthesized by sequential addition of CMS and styrene.

Figure 3:
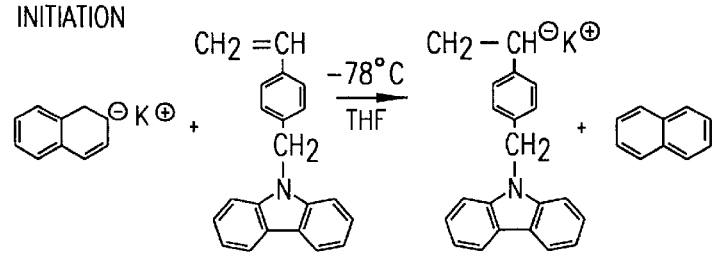
FIG. 3 shows a reaction scheme of anionic polymerization used in the present invention.
Figure 3:
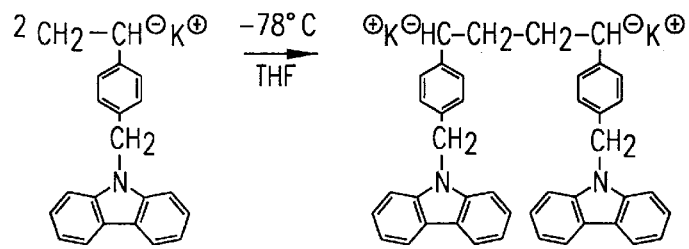
Figure 3:
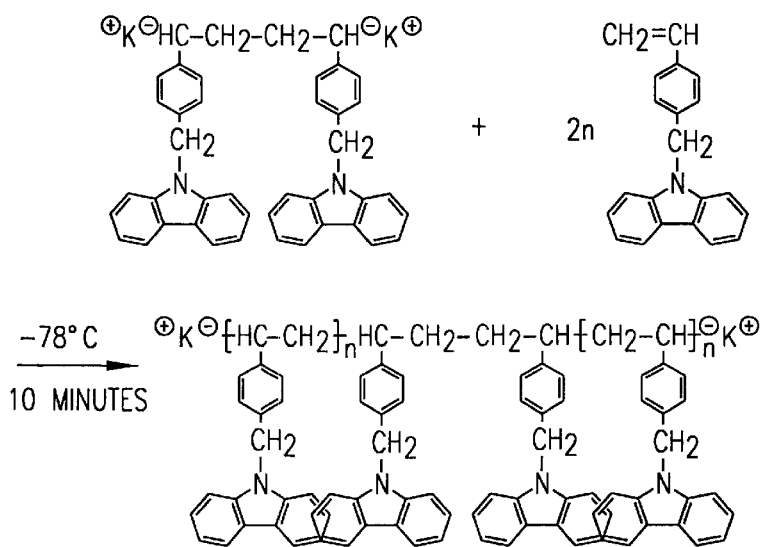
Figure 3:
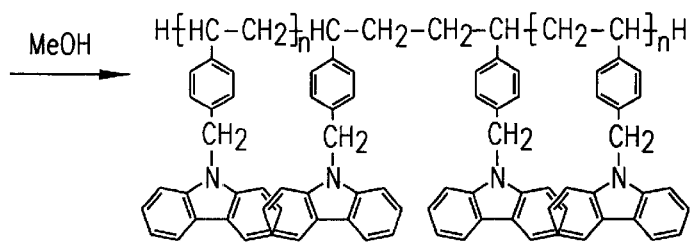

A reaction scheme of high molecular weight polymer of the present invention according to the anionic polymerization method can be seen in FIG. 3.

A better understanding of the present invention may be obtained in light of the following examples which are set forth to illustrate, but are not to be construed to limit the present invention.

EXAMPLES 1–9

Synthesis of Homopolymer of CMS at −45° C. and −78° C.

TABLE 1

CMS HOMOPOLYMER SYNTHESIZED AT −45° C. and −78° C.

| Run | Reaction Conc. (mmol) K-Naph | CMS | Time (min) | Temp. (° C.) | Yield (%) | Molecular Weight (MW) Calcd | obsd | MW Distribution |
|---|---|---|---|---|---|---|---|---|
| 1 | 0.099 | 1.715 | 10 | −45 | 49.2 | 4.800 | 8.600 | 2.05 |
| 2 | 0.100 | 1.731 | 20 | −45 | 54.8 | 5.400 | 9.900 | 2.09 |
| 3 | 0.102 | 1.700 | 30 | −45 | 64.1 | 6.100 | 10.700 | 2.04 |
| 4 | 0.099 | 1.667 | 120 | −45 | 67.2 | 6.400 | 10.000 | 2.11 |
| 5 | 0.095 | 1.613 | 10 | −78 | 91.0 | 8.700 | 9.600 | 1.67 |
| 6 | 0.097 | 1.686 | 20 | −78 | 93.3 | 9.200 | 9.700 | 1.58 |
| 7 | 0.104 | 1.819 | 30 | −78 | 97.3 | 9.700 | 9.500 | 1.65 |
| 8 | 0.096 | 1.536 | 24h | −78 | 98.0 | 8.900 | 8.800 | 1.55 |
| 9 | 0.094 | 1.766 | 10 | −78 | 96.0 | 10.600 | 9.300 | 1.28 |

CMS is soluble in a wide range of organic solvents such as DMF(N,N-dimethylformamide), DMSO (dimethylsulfoxide), THF(tetrahydrofuran) and so on. However, it is insoluble in most nonpolar solvents such as hexane, benzene etc. The polymerization of CMS was attempted with K-Naph. in THF at either −45 or −78° C. In each case, the reaction mixture always showed a deep red color during the course of the polymerization. The characteristic red color indicates the formation of styryl anion derived from CMS. The red color remained in THF even after 24 h, however, it immediately disappeared upon addition of a small amount of methanol to quench the polymerization, indicating the existence of the living ends.

Table 1 shows the homopolymerization results of CMS in THF at −45° C. under high vacuum condition. The yields of the polymer levels up after 30 min. The MWD(Molecular Weight Distribution) of PCMS was broad, about 2.0, and SEC curve of PCMS has shoulder. Also, the observed molecular weight is higher than the calculated value from [M]/[I] ratios.

In the anionic polymerization of (3-vinylphenyl)methyl methyl sulfide, reported by Nakahama et al, gelled polymeric materials were obtained during polymerization in THF at −78° C. due to the radical combination, induced by 1,6-elimination at the reactive chain end, to form a crosslinked network. Also, Nakahama et al. reported the polymerization results of hexynylstyrene derivatives at higher temperature, 20 and 40° C. The SEC curve showed multimodal peaks due to the proton abstraction after the completion of the polymerization. However, there is no crosslink reaction observed during and after polymerization of CMS. This means there is no radical forming reaction during polymerization. Therefore, it may be due to the undesirable side reaction such as the methylene proton abstraction by reactive chain end in THF at −45° C. The propagating chain end derived from PCMS is deactivated at −45° C. Probably, the reason of this deactivation is the proton abstraction from the methylene group of the CMS, because the proton is known to be acidic.

Table 1 also shows the homopolymerization results of CMS in THF at −78° C. under high vacuum condition. The yields of the polymers in THF at −78° C. rapidly increased in the initiation step. The yield reached 91.0% within 10 min but slowly increased to 98.0% within 1 day. It may be due to the crystallization of the monomer at −78° C. during the polymerization, and slowly dissolved again in THF. Therefore, it takes long time to get 100% yield. The observed molecular weight of the polymer was in good agreement with the calculated molecular weight. However, the MWD is still broad even when polymerization was carried out at low temperature due to both the crystallization of the monomer leading to inhomogeneous solution during the polymerization and the side reaction. Therefore, it is highly difficult to get narrow MWD even in dilute solution. However, still unimodal peak was observed without shoulder. It appears that any possible side reactions mentioned in previous could be eliminated or reduced at −78° C.

Figure 4:
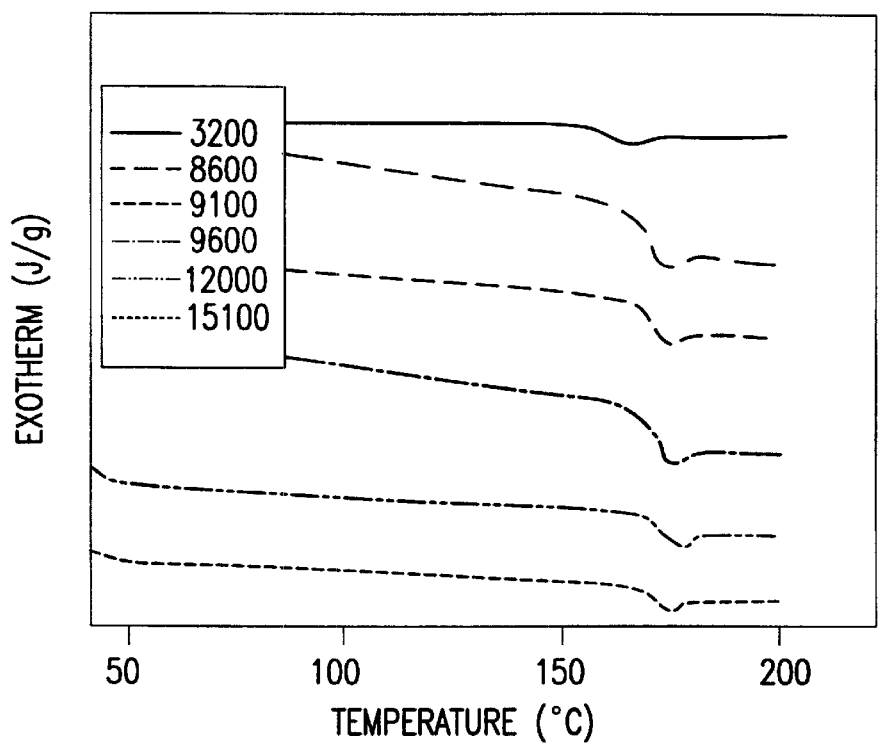
FIG. 4 shows a TGA curve of thermal properties of the synthesized polymer in the present invention.
Figure 5:
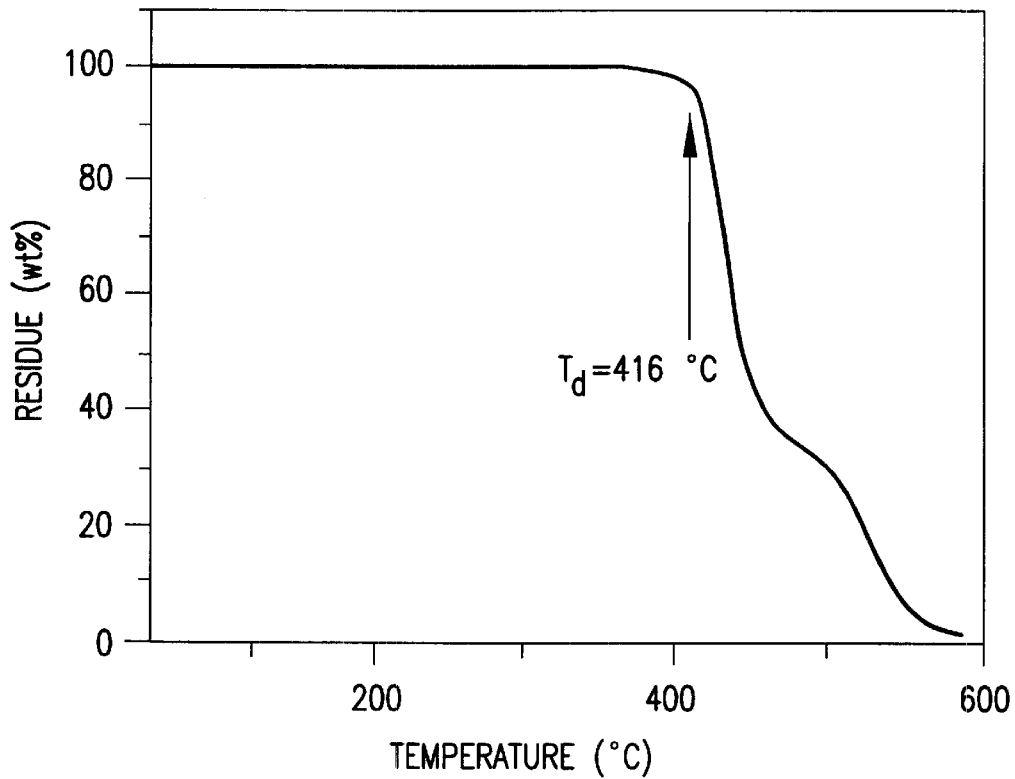
FIG. 5 shows DSC curves of thermal properties of the synthesized polymer in the present invention.

The thermal properties of the synthesized homopolymer was measured by use of differential scanning calorimeter (DSC) and thermo gravimetric analysis (TGA) The results are shown in FIGS. 4 and 5. By using TGA, the decomposition temperature of the polymer was found to be 416 C, at which weight loss of 5 wt % occurs, as best seen in FIG. 4.

The glass transition temperature was measured using DSC, and the temperature was seen to change from 159 C to 173 C, depending on the molecular weight, as seen in FIG. 5. The prepared polymer has more thermally stable structure than polystyrene polymer, because polystyrene polymer has a decomposition temperature of 304 C and a glass transition temperature of 100 C.

From Table 2, when the molecular weight is 3,000 or more, the glass transition temperature exceeds 150 C. When the molecular weight is 10,000 or more, the temperature becomes constant at 173 C, though the glass transition temperature depends on the molecular weight.

TABLE 2

CHANGE OF GLASS TRANSITION TEMPERATURE OF HOMOPOLYMER ACCORDING TO MOLECULAR WEIGHT

| Molecular weight | 3,200 | 8,600 | 9,100 | 9,600 | 12,000 | 15,000 |
|---|---|---|---|---|---|---|
| Glass Transition Temp. (° C.) | 159 | 169 | 171 | 171 | 173 | 173 |

Figure 6:
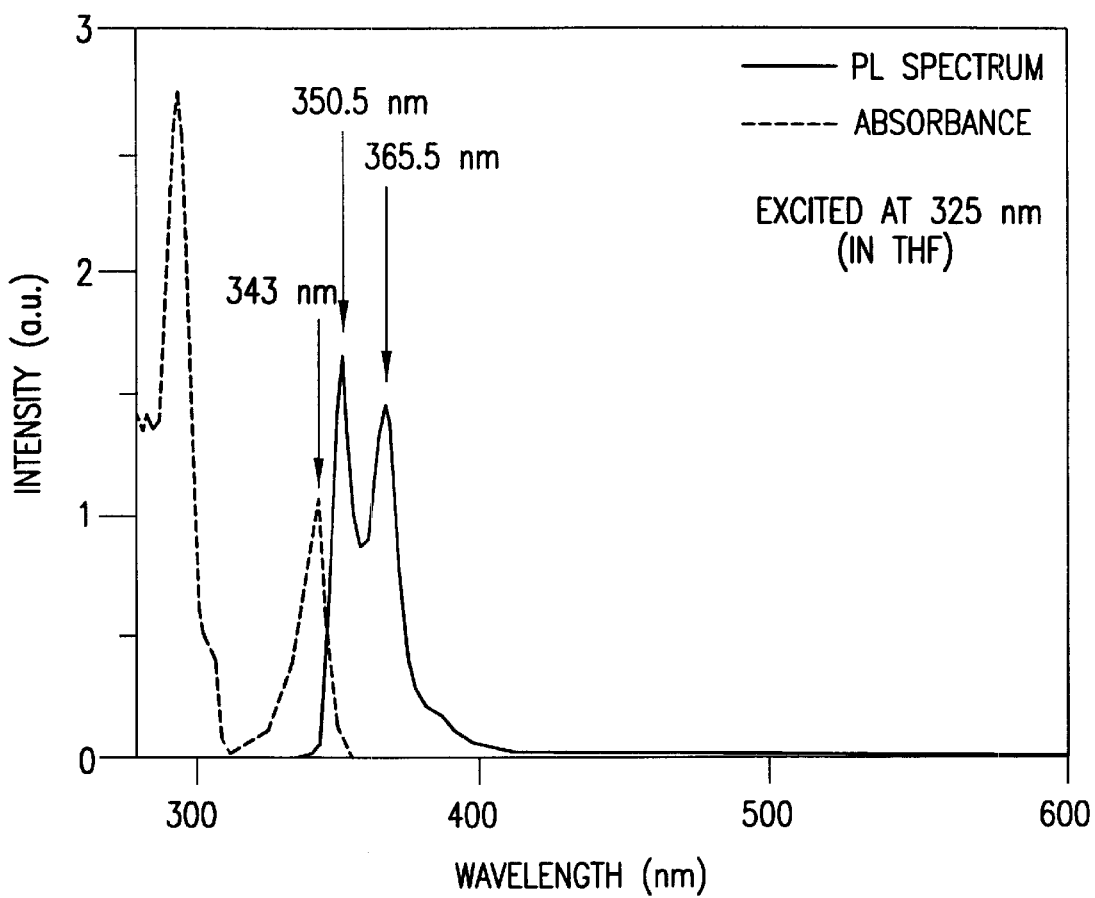
FIG. 6 shows spectra of photoluminescence properties of homopolymer synthesized in the present invention.

CMS synthesized in the present invention has luminescent properties, and is excited at a wavelength of 325 nm by use of He—Cd laser, whereby the luminescence peak is seen at 350.5 nm and 365.5 nm, as can be shown in FIG. 6.

EXAMPLES 10–13

Synthesis of Copolymer of CMS and Styrene or Other Monomer

TABLE 3

PROPERTIES OF COPOLYMER SYNTHESIZED FROM CMS AND STYRENE OR OTHER MONOMERS

| | Reaction Con. (mmol) | | | | | | Time | Temp. | Yield | MW | | MW |
|---|---|---|---|---|---|---|---|---|---|---|---|---|
| Run | K-Naph | CMS | Styrene | DPE | MMA | CzMA | (min) | (° C.) | (%) | calc'd | obsd | Dis. |
| 10 | 0.091 | 2.030 | 5.552 | | | | 120 | −78 | 100 | 25.700 | 27.000 | 1.51 |
| 11 | 0.104 | 0.839 | 5.437 | | | | 120 | −78 | 100 | 16.000 | 17.000 | 1.47 |
| 12 | 0.130 | 2.153 | | 0.153 | 5.106 | | 300 | −78 | 98 | 17.500 | 20.000 | 1.48 |
| 13 | 0.111 | 2.158 | | 0.122 | | 2.129 | 300 | −78 | 100 | 22.000 | 23.000 | 1.48 |

EXAMPLE 10

First Added Monomer-CMS, Second Added Monomer-Styrene

EXAMPLE 11

First Added Monomer-Styrene, Second Added Monomer-CMS

From the result of Table 3, it can be seen that, after CMS is homopolymerized, useful as the second added monomer, styrene, methylmethacylate (MMA) or 9-ethylcarbazollyl methacylate (CzMA) is added, thereby synthesizing a block copolymer. This means that the second monomer is added to reactive terminals of CMS to further perform a polymerization. From the synthesis of the block copolymer of CMS and styrene, it can be confirmed that the block copolymer is synthesized regardless of addition order of CMS and styrene to the reaction. Accordingly, reactivity of CMS and styrene is assumed to be similar. Also, it is seen from the data of the block copolymers of CMS and MMA or CzMA that the reactivity of CMS is larger than that of MMA and CZMA.

In accordance with the method of the present invention, a homopolymer and a block copolymer can be synthesized by use of a solid styrene monomer containing carbazole.

The polymer of the present invention synthesized from carbazole-containing monomers with optical properties is advantageous in terms of various optical properties, limited molecular weight distribution, and improved thermal stability and solubility. Accordingly, the temperature is decreased on polymerization and thus side-reactions are minimized, so that the solid monomer can be synthesized according to the method of the present invention.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method for synthesizing functionalized styrene derivatives containing carbazole comprising the steps of:
   (a) reacting carbazole with a vinylbenzyl chloride solution to produce 4-(9-carbazolyl) methylstyrene in solution;
   (b) extracting said 4-(9-carbazolyl) methylstyrene from said solution;
   (c) dissolving said 4-(9-carbazolyl) methylstyrene in tetrahydrofuran;
   (d) adding said solution of 4-(9-carbazolyl) methylstyrene in tetrahydrofuran to a solution of K-naphthalenide in tetrahydrofuran to produce poly(4-(9-carbazollylmethylstyrene)).

2. A method for synthesizing a block copolymer of 4-methylcarbazollyistyrene comprising the steps of:
   (a) polymerizing styrene with a solution of K-naphthalenide in tetrahydrofuran to produce a living homopolystyryl solution;
   (b) adding 4-(9-carbazolyl) methylstyrene to said living homopolystyryl solution to form PCMS-b-PS-b-PCMS (poly(4-(9-carbazolyl) methylstyrene)-block-polystyrene-block-poly (4-(9-carbazolyl methylstyrene)).

3. A method for synthesizing a block copolymer of styrene comprising the steps of:
   (a) polymerizing 4-(9-carbazolyl) methylstyrene with a solution of K-naphthalenide in tetrahydrofuran to produce a living homopoly (4-(9-carbazolyl) methylstyrene) solution;
   (b) adding styrene to said living homopoly (4-(9-carbazolyl) methylstyrene) solution to form PS-b-PCMS-b-PS(polystyrene-block-poly(4-(9-carbazolyl) methylstyrene)-block-polystyrene).

4. The method for synthesizing functionalized styrene derivatives containing carbazole as recited in claim 1 wherein said step of reacting carbazole is performed at a temperature of −78° C.

5. The method for synthesizing a block copolymer of 4-(9-carbazolyl) methylstyrene as recited in claim 2 wherein said step of polymerizing styrene with a solution of K-naphthalenide in tetrahydrofuran is performed at a temperature of −78° C.

6. The method for synthesizing a block copolymer of styrene as recited in claim 2 wherein said step of polymerizing 4-(9-carbazolyl) methylstyrene with a solution of K-naphthalenide in tetrahydrofuran is performed at a temperature of −78° C.

* * * * *